US009204860B2

(12) United States Patent
Ji et al.

(10) Patent No.: US 9,204,860 B2
(45) Date of Patent: Dec. 8, 2015

(54) ULTRASOUND DETECTING SYSTEM AND METHOD AND APPARATUS FOR AUTOMATICALLY CONTROLLING FREEZE THEREOF

(71) Applicant: GE Medical Systems Global Technology Company, LLC, Waukesha, WI (US)

(72) Inventors: Kai Ji, Wuxi (CN); Linhai Xue, Jiangsu (CN)

(73) Assignee: GE MEDICAL SYSTEMS TECHNOLOGY COMPANY, LLC, Waukesha, WI (US)

( * ) Notice: Subject to any disclaimer, the term of this patent is extended or adjusted under 35 U.S.C. 154(b) by 565 days.

(21) Appl. No.: 13/629,672

(22) Filed: Sep. 28, 2012

(65) Prior Publication Data

US 2013/0083629 A1  Apr. 4, 2013

(30) Foreign Application Priority Data

Sep. 30, 2011 (CN) .......................... 2011 1 0312486

(51) Int. Cl.
*G01S 15/02* (2006.01)
*A61B 8/00* (2006.01)
*G01S 7/52* (2006.01)
*A61B 8/08* (2006.01)

(52) U.S. Cl.
CPC .............. *A61B 8/4254* (2013.01); *A61B 8/4263* (2013.01); *A61B 8/4433* (2013.01); *A61B 8/54* (2013.01); *G01S 7/52096* (2013.01); *A61B 8/08* (2013.01)

(58) Field of Classification Search
CPC ...... A61B 8/4254; A61B 8/4433; A61B 8/54; A61B 8/4263; A61B 8/08; G01S 7/52096
USPC .......................................................... 367/105
See application file for complete search history.

(56) References Cited

U.S. PATENT DOCUMENTS

| | | | |
|---|---|---|---|
| 8,330,741 B1 * | 12/2012 | Camarota ...................... 345/174 |
| 8,892,191 B2 * | 11/2014 | Brennan et al. ............... 600/476 |
| 8,903,475 B2 * | 12/2014 | Brennan et al. ............... 600/476 |
| 8,903,476 B2 * | 12/2014 | Brennan et al. ............... 600/476 |
| 8,914,098 B2 * | 12/2014 | Brennan et al. ............... 600/478 |
| 2008/0278439 A1 * | 11/2008 | Huang et al. .................. 345/156 |

(Continued)

FOREIGN PATENT DOCUMENTS

| | | |
|---|---|---|
| CN | 1834691 A | 9/2006 |
| CN | 101884543 A | 11/2010 |
| JP | 2013081766 A * | 5/2013 |

OTHER PUBLICATIONS

Unofficial translation of Chinese Search Report issued in connection with corresponding CN Application No. 201110312486.9 dated Jul. 15, 2015.

*Primary Examiner* — Daniel Pihulic
(74) *Attorney, Agent, or Firm* — GE Global Patent Operation; Marc A. Vivenzio

(57) ABSTRACT

An apparatus for automatically controlling a state of operation of an ultrasound detecting system is provided. The apparatus comprises a first sensor disposed in a probe of the ultrasound detecting system and connected to a device main body, wherein the first sensor is configured to detect if the probe is being operated, and a control unit configured to control the state of operation of the ultrasound detecting system based on the detecting results of the first sensor.

14 Claims, 2 Drawing Sheets

(56) References Cited

U.S. PATENT DOCUMENTS

| | | | |
|---|---|---|---|
| 2010/0228119 A1* | 9/2010 | Brennan et al. | 600/424 |
| 2010/0228123 A1* | 9/2010 | Brennan et al. | 600/437 |
| 2010/0228124 A1* | 9/2010 | Brennan et al. | 600/437 |
| 2010/0228132 A1* | 9/2010 | Brennan et al. | 600/478 |
| 2010/0228238 A1* | 9/2010 | Brennan et al. | 606/13 |
| 2010/0292577 A1 | 11/2010 | Sato et al. | |
| 2013/0083629 A1* | 4/2013 | Ji et al. | 367/95 |
| 2013/0147770 A1* | 6/2013 | Dahl et al. | 345/177 |

\* cited by examiner

ULTRASOUND DETECTING SYSTEM AND METHOD AND APPARATUS FOR AUTOMATICALLY CONTROLLING FREEZE THEREOF

BACKGROUND OF THE INVENTION

Embodiments of the present invention generally relate to an ultrasound detecting system, and more particularly, relate to an ultrasound detecting system and method and apparatus for automatically controlling freeze thereof.

For energy saving, some ultrasound detecting systems normally have an auto-freeze function. This function will enable an ultrasound system to freeze the scan of an ultrasound probe automatically after a certain period of no operation on a user interface, so as to save energy and extend the life of the probe. This period to be waited before performing freeze is defined through experience. However, no energy savings can be realized during this waiting period.

Moreover, this technique of auto-freeze is not accurate. For example, when a user stops operation on the user interface, he/she is actually conducting other operations so as to obtain a better image. Thus, when the time for no operation on a user interface exceeds the prescribed value, the scan of a probe will be mistakenly frozen. Hence, a method and apparatus that can accurately control the freeze of a probe are needed.

BRIEF SUMMARY OF THE INVENTION

An apparatus for automatically controlling a state of operation of an ultrasound detecting system is provided. The apparatus comprises a first sensor disposed in a probe of the ultrasound detecting system and connected to a device main body, wherein the first sensor is configured to detect if the probe is being operated, and a control unit configured to control the state of operation of the ultrasound detecting system based on the detecting results of the first sensor.

According to another embodiment of the present invention, an ultrasound detecting system is provided. The system comprises a device main body, a probe connected to the device main body; and an apparatus for automatically controlling a state of operation of the ultrasound detecting system. The apparatus comprises a first sensor disposed in the probe and connected to a device main body, wherein the first sensor is configured to detect if the probe is being operated, and a control unit configured to control the state of operation of the ultrasound detecting system based on detecting results of the first sensor.

According to another embodiment of the present invention, a method for automatically controlling a state of operation of an ultrasound detecting system is provided. The method comprises detecting, with a first sensor disposed in a probe of the ultrasound detecting system, if the probe is being operated, and automatically controlling the state of operation of the ultrasound detecting system based on the results of detecting if the probe is being operated.

BRIEF DESCRIPTION OF THE DRAWINGS

In order to more thoroughly understand the disclosure of the present invention, the detailed description is made below in combination with the following drawings, wherein.

DETAILED DESCRIPTION OF THE INVENTION

Specific embodiments of the invention will be described in detail below, but the invention is not limited to the following specific embodiments.

Embodiments of the present invention use a proximity sensor that is installed in a probe and/or an ultrasound detecting system to detect whether a user is operating the probe or approaching the ultrasound detecting system. The proximity sensor is a sensor that is used to detect a difference in capacitance, inductance or other physical quantities between non-contact conditions and proximity conditions. More particularly, capacitive sensors are becoming more and more popular in the field of touch panels, and a touch panel of a notebook is generally designed based on this technique.

Figure 1:
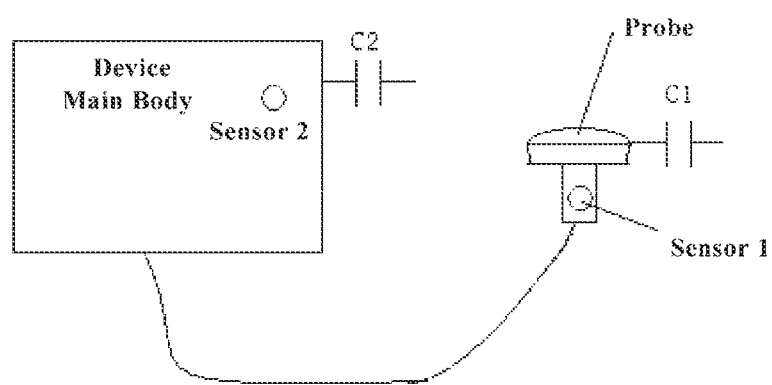
FIG. 1 schematically shows a composition of an ultrasound detecting system according to an embodiment of the invention.

FIG. 1 schematically shows a composition of an ultrasound detecting system according to an embodiment of the invention. The ultrasound detecting system comprises two parts: a device main body and an ultrasound probe, wherein the ultrasound is connected to the device main body via a cable. In the embodiment as shown in FIG. 1, the ultrasound detecting system further comprises sensor 1 and sensor 2, wherein, sensor 1 is located in a probe, and sensor 2 is located in a device main body. Here, the expression "located in a probe" means that sensor 1 is attached to or embedded in a case of the probe or is located inside the probe. Similarly, the expression "located in a device main body" means that sensor 2 is attached to or embedded in a case of the device main body or is located inside the device main body.

Sensor 1 and sensor 2 are proximity sensors that are used to detect approaching of positions. In at least one embodiment of the invention, proximity sensors 1 and 2 are configured to detect approaching and departing of a user relative to an ultrasound detecting system. Specifically, sensor 1 detects whether a probe is being operated by detecting whether the probe is being approached or held by a user, and sensor 2 is used to detect whether there is a user in the proximity of a device main body.

In an embodiment of the invention, proximity sensors 1 and 2 are capacitive sensors, which sense changes of capacitance. Specifically, sensor 1 in a probe senses changes of capacitance C1 (as shown by FIG. 1) between the probe and ambient environment. When a user's hand or other body parts approach or hold the probe, the value of C1 will increase; on the contrary, when the user's hand or other body parts depart or release the probe, the value of C1 will decrease. Sensor 2 in a device main body senses changes of capacitance C2 (as shown by FIG. 1) between the device main body and ambient environment. Similarly, when the user approaches the device main body, the value of C2 will increase; when the user departs the device main body, the value of C2 will decrease.

Hence, through detecting changes in the values of C1 and C2, sensors 1 and 2 can readily determine whether the probe is being operated and whether there is a user in proximity of the device main body. When the value of C1 is detected to increase, it is indicated that the user or the user's body parts are approaching the probe, i.e., the probe is being, or about to be, operated. On the contrary, when the value of C1 is detected to decrease, it is indicated that the user or the user's body parts are departing the probe, i.e., the probe is not being operated. Similarly, when the value of C2 is detected to increase, it is indicated that the user is approaching the device main body. On the contrary, when the value of C2 is detected to decrease, it is indicated that the user is departing the device main body.

In an embodiment, the reference values of C1 and C2, which are preset for sensors 1 and 2 through experience or experimentation respectively, are taken as the threshold values. When sensor 1 detects that the value of C1 changes to be greater than the preset threshold value, it is indicated that the probe is being operated; on the contrary, when sensor 1 detects that the value of C1 changes to be smaller than the preset threshold value, it is indicated that the probe is not operated. Similarly, when sensor 2 detects that the value of C2 changes to be greater than the preset threshold value, it is indicated that the user is in proximity of the device main body; on the contrary, when sensor 2 detects that the value of C2 changes to be smaller than the preset threshold value, it is indicated that the user has departed the device main body. The respective threshold values of sensors 1 and 2 can be identical or different. In addition, sensors 1 and 2 can be further set with two threshold values, i.e., a first threshold value and a second threshold value, wherein the first threshold value is greater than the second threshold value. When the measured value is greater than the first threshold value, it is indicated that the probe is being operated or the user is in proximity. When the measured value is smaller than the second threshold value, it is indicated that the probe is not operated or the user is not in proximity.

In another embodiment, sensors 1 and 2 detect the variable quantities of the values of C1 and C2. The variable quantity threshold values are preset for sensors 1 and 2, respectively. When sensor 1 detects that the increasing quantity of the C1 value exceeds the variable quantity threshold value of sensor 1, it is indicated that the probe is being held, i.e., being operated. When sensor 1 detects that the decreasing quantity of the C1 value exceeds the variable quantity threshold value, it is indicated that the user or the user's body parts are departing the probe, i.e., the probe is not being operated. Similarly, when sensor 2 detects that the increasing quantity of the C2 value exceeds the variable quantity threshold value of sensor 2, it is indicated that the user is approaching the device main body to the proximity of the device main body. When sensor 2 detects that the decreasing quantity of the C2 value exceeds the variable quantity threshold value of sensor 2, it is indicated that the user has departed the device main body, i.e., is not in proximity of the device main body. Alternatively, each sensor can be set with an increasing quantity threshold value and a decreasing quantity threshold value, respectively.

In another embodiment of the invention, proximity sensors 1 and 2 are inductive sensors, which sense changes of inductance in a manner similar to the above manner. Specifically, sensor 1 in a probe senses changes of inductance L1 between the probe and ambient environment. When a user's hand or other body parts approach or holds the probe, the value of L1 will increase; on the contrary, when the user's hand or other body parts depart or release the probe, the value of L1 will decrease. Sensor 2 in a device main body senses changes of inductance L2 between the device main body and ambient environment. Similarly, when the user approaches the device main body, the value of L2 will increase; when the user departs the device main body, the value of L2 will decrease.

Hence, through detecting changes in the values of L1 and L2, sensors 1 and 2 can readily determine whether the probe is being operated and whether there is a user in proximity of the device main body. When the value of L1 is detected to increase, it is indicated that the user or the user's body parts are approaching the probe, i.e., the probe is being, or is about to be, operated. On the contrary, when the value of L1 is detected to decrease, it is indicated that the user or the user's body parts are departing the probe, i.e., the probe is not being operated. Similarly, when the value of L2 is detected to increase, it is indicated that the user is approaching the device main body. On the contrary, when the value of L2 is detected to decrease, it is indicated that the user is departing the device main body.

In an embodiment, the reference values of L1 and L2, which are preset for sensors 1 and 2 through experience or experimentation respectively, are taken as the threshold values. When sensor 1 detects that the value of L1 changes to be greater than the preset threshold value, it is indicated that the probe is being operated; on the contrary, when sensor 1 detects that the value of L1 changes to be smaller than the preset threshold value, it is indicated that the probe is not being operated. Similarly, when sensor 2 detects that the value of L2 changes to be greater than the preset threshold value, it is indicated that the user is in proximity of the device main body; on the contrary, when sensor 2 detects that the value of L2 changes to be smaller than the preset threshold value, it is indicated that the user has departed the device main body. The respective threshold values of sensors 1 and 2 can be identical or different. In addition, each of sensors 1 and 2 can be further set with two threshold values, i.e., a first threshold value and a second threshold value, wherein the first threshold value is greater than the second threshold value. When the measured value is greater than the first threshold value, it is indicated that the probe is being operated or the user is in proximity; when the measured value is smaller than the second threshold value, it is indicated that the probe is not operated or the user is not in proximity.

In another embodiment, sensors 1 and 2 detect the variable quantities of the values of L1 and L2. The variable quantity threshold values are preset for sensors 1 and 2, respectively. When sensor 1 detects that the increasing quantity of the L1 value exceeds the variable quantity threshold value of sensor 1, it is indicated that the probe is being held, i.e., being operated. When sensor 1 detects that the decreasing quantity of the L1 value exceeds the variable quantity threshold value, it is indicated that the user or the user's body parts are departing the probe, i.e., the probe is not being operated. Similarly, when sensor 2 detects that the increasing quantity of the L2 value exceeds the variable quantity threshold value of sensor 2, it is indicated that the user is approaching the device main body to the proximity of the device main body. When sensor 2 detects that the decreasing quantity of the L2 value exceeds the variable quantity threshold value of sensor 2, it is indicated that the user has departed the device main body, i.e., is not in proximity of the device main body. Alternatively, each sensor can be also set with an increasing quantity threshold value and a decreasing quantity threshold value, respectively.

The above embodiments take capacitive sensors and inductive sensors as examples and make a detailed description. However, persons skilled in the art will appreciate that sensors 1 and 2 can also be other types of sensors, as long as they can detect whether a probe is being operated and whether there is a user in proximity of a device main body. In addition, sensors 1 and 2 can also be different from each other, for example, one is a capacitive sensor, and another is an inductive sensor.

Sensors 1 and 2 send their respective detecting results to a control unit of an ultrasound detecting system (not shown), and then the control unit performs operation of freeze controlling on the ultrasound detecting system based on the detecting results of sensors 1 and 2. In an embodiment of the invention, the control unit puts the probe in a frozen state when sensor 1 detects that the probe is not operated, without necessarily waiting a certain period, thereby reducing energy consumption. In such an embodiment, in fact another sensor 2 can be omitted.

In another embodiment, the control unit can put the probe in a frozen state only when sensor 1 detects that the probe is not operated and sensor 2 detects there is no user in the proximity of the device main body. The operation of freeze as performed by the control unit on the ultrasound detecting system is to freeze the probe. Alternatively, the control unit can also enable the ultrasound detecting system to be in standby state. Through this control method, accurate freeze controlling can be realized. Through this method, even if a user does not operate a probe or an ultrasound detecting system for a long period, but is still in the proximity of a device main body, for example, makes other preparation operations for later scans, the probe will not be frozen. Although sensor 1 detects that the probe is not operated, sensor 2 detects that the user is still in proximity of the device main body. Hence, the control unit will not freeze the probe. In an embodiment, in this situation, the operation of freeze as performed by the control unit on the ultrasound detecting system is not to freeze the probe so as to enable the ultrasound detecting system to be in an activated state.

In the above description, sensor 1 for detecting whether a probe is operated and sensor 2 for detecting whether a user is in the proximity of a device main body comprise one sensor, respectively. However, those persons skilled in the art will appreciate that this is only an example embodiment of the invention; in fact, sensor 1 for detecting whether a probe is operated and sensor 2 for detecting whether a user is in the proximity of a device main body can each comprise a plurality of sensors, and the plurality of sensors can be the same or different types of sensors.

During the period when a probe is in a frozen state: if sensor 2 detects that a user is approaching a device main body, a control unit operates so as to activate an ultrasound detecting system, and waits for detecting results of sensor 1, instead of unfreezing the probe immediately; if sensor 1 detects that the user or the user's body parts are approaching the probe, the control unit activates the ultrasound detecting system and unfreezes the probe. In an embodiment, if sensor 1 detects that the user or the user's body parts are approaching the probe during the freeze period of the probe, the control unit activates the ultrasound detecting system and freezes the probe, regardless of detecting results of sensor 2. In another embodiment, release of the frozen state of the probe must be realized manually by the user, for example, by pressing a certain button or switch on the ultrasound detecting system or implementing other operations on the ultrasound detecting system.

The above described sensors 1 and 2 as well as the control unit can be deemed as components that constitute an apparatus for automatically controlling freeze/unfreeze of a probe of an ultrasound detecting system.

Figure 2:
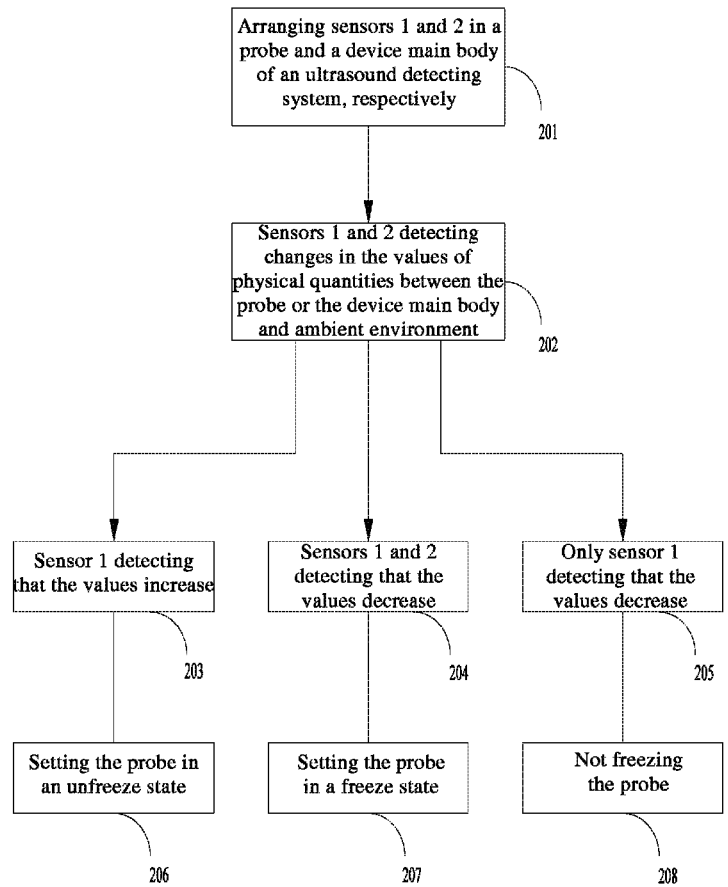
FIG. 2 provides a flow chart for a method for automatically controlling freeze/unfreeze of a probe according to an embodiment of the invention.

FIG. 2 provides a flow chart for a method for automatically controlling freeze/unfreeze of a probe according to an embodiment of the invention.

In step 201, sensors 1 and 2 are arranged in a probe and a device main body of an ultrasound detecting system, respectively (see FIG. 1).

In step 202, sensors 1 and 2 detect changes (increasing or decreasing) in the values of a physical quantity such as capacitance or inductance between the probe or the device main body and ambient environment.

If sensor 1 detects that the value of the physical quantity increases (step 203), the probe will be set in an activated (unfrozen) state (step 206). Here, no matter whether sensor 2 detects changes or what changes occur, as long as sensor 1 detects that the value increases, the probe will be set in an unfrozen state.

If both sensors 1 and 2 detect that the values of the physical quantity decrease (step 204), the probe will be set in a frozen state (step 207). Alternatively, the ultrasound detecting system can also be set in standby state at the same time.

If only sensor 1 detects that the value of the physical quantity decreases, while sensor 2 detects that the value does not change obviously or increase (step 205), the ultrasound detecting system will be set in an activated state, with the probe being unfrozen (step 208).

As described above, sensors 1 and 2 can also be set with one or more threshold values for measured value or variable quantity, so as to make more accurate judgments. Here, no unnecessary repetitions are provided.

When an operator touches, approaches or departs a probe or a device main body of an ultrasound detecting system, an environmental physical quantity such as capacitance or inductance between the probe or the device main body and environment will undergo changes. Hence, freeze/unfreeze of scanning can be triggered by using these changes, thereby realizing energy savings of the system.

According to an embodiment of the invention, the sensor determines whether the probe is being operated by detecting changes in capacitance between the probe and ambient environment.

According to an embodiment of the invention, the sensor determines whether the probe is being operated by detecting changes in inductance between the probe and ambient environment.

According to an embodiment of the invention, the control unit performs operation of freeze controlling when the first sensor detects that the probe is not being operated, and the operation of freeze controlling as performed herein is to freeze the probe.

According to an embodiment of the invention, the apparatus for automatically controlling freeze further comprises a second sensor that is disposed in the device main body of the ultrasound detecting system, the second sensor being used to detect whether a user is being in the proximity of the device main body.

According to an embodiment of the invention, the control unit performs operation of freeze controlling when the first sensor detects that the probe is not being operated and the second sensor detects that the user is not being in the proximity of the device main body, and the operation of freeze controlling as performed herein is to freeze the probe.

According to an embodiment of the invention, the operation of freeze controlling as performed by the control unit when the first sensor detects that the probe is not being operated and the second sensor detects that the user is not being in the proximity of the device main body, further comprises enabling the ultrasound detecting system to be in a standby state.

According to an embodiment of the invention, the control unit performs operation of freeze controlling when the first sensor detects that the probe is not being operated but the second sensor detects that the user is in the proximity of the device main body; and the operation of freeze controlling as performed herein is not to freeze the probe so as to enable the ultrasound detecting system to be in an activated state.

According to an embodiment of the invention, the step of using the first sensor to detect whether the probe is being operated comprises using the first sensor to determine whether the probe is being operated by detecting changes in capacitance between the probe and ambient environment.

According to an embodiment of the invention, the step of using the first sensor to detect whether the probe is being operated comprises using the first sensor to determine whether the probe is being operated by detecting changes in inductance between the probe and ambient environment.

According to an embodiment of the invention, the step of automatically performing operation of freeze controlling on the ultrasound detecting system based on detecting results of the first sensor comprises: performing operation of freeze controlling when using the first sensor to detect that the probe is not being operated, the operation of freeze controlling as performed herein being to freeze the probe.

According to an embodiment of the invention, the step of automatically performing operation of freeze controlling on the ultrasound detecting system based on detecting results of the sensor comprises: performing operation of freeze controlling when using the first sensor to detect that the probe is being operated and using a second sensor to detect that the user is being in the proximity of the device main body, the operation of freeze controlling as performed herein being to freeze the probe.

According to an embodiment of the invention, the operation of freeze controlling as performed when using the first sensor to detect that the probe is not being operated and using the second sensor to detect that the user is not being in the proximity of the device main body, further comprises enabling the ultrasound detecting system to be in a standby state.

According to an embodiment of the invention, further comprise the step of: performing operation of freeze controlling when using the first sensor to detect that the probe is not being operated but using the second sensor to detect that the user is being in the proximity of the device main body, the operation of freeze controlling as performed herein being not to freeze the probe so as to enable the ultrasound detecting system to be in an activated state.

Through the apparatus, method or system of the invention, as long as a doctor does not operate a probe, an ultrasound system can smartly stop scanning (freeze the probe), without necessarily waiting a predetermined period. In addition, by combining a first sensor and a second sensor, it can be accurately known whether a use wishes no operation of a probe or makes preparations for next scanning so as to automatically and smartly control freeze of the probe.

Furthermore, through the second sensor as mentioned above that is disposed in a device main body of an ultrasound detecting system, when it is detected that a user does not operate a probe and is not in the proximity of the device main body, the ultrasound detecting system may be automatically controlled into a standby state, thereby saving more energy.

Embodiments of the invention are easy to implement, for the reason that the algorithm thereof is very simple and efficient. In the prior art, to determine whether a probe is being operated, it is very complex, hard to implement and difficult to calculate a difference of ultrasound data between patient scanning and air scanning. In addition, the invention reflects a doctor's operations, i.e., whether the doctor is holding a probe and approaching a system. Furthermore, embodiments of the present invention can reduce manual control of freeze/unfreeze, because the invention can enable the freeze/unfreeze to be fully automatic.

Although specific embodiments of the invention have been described above in combination with drawings, without deviating from the spirit and range of the invention, those persons skilled in the art can make various changes, amendments or equivalent alternations to the invention. These changes, amendments or equivalent alternations will be deemed as falling within the scope of the invention as defined by the claims as attached herein.

What is claimed is:

1. An apparatus for automatically controlling a state of operation of an ultrasound detecting system, the apparatus comprising:
a first sensor disposed in a probe of the ultrasound detecting system and connected to a device main body, wherein the first sensor is configured to detect if the probe is being operated;
a second sensor disposed in the device main body of the ultrasound detecting system, wherein the second sensor is configured to detect if a user is in proximity of the device main body; and
a control unit configured to control the state of operation of the ultrasound detecting system based on the detecting results of the first sensor, wherein the control unit is further configured to set the probe in an activated state when the first sensor detects that the probe is not being operated and when the second sensor detects that the user is in proximity of the device main body.

2. The apparatus according to claim 1, wherein the first sensor detects if the probe is being operated by detecting changes in capacitance between the probe and the ambient environment.

3. The apparatus according to claim 1, wherein the first sensor detects if the probe is being operated by detecting changes in inductance between the probe and the ambient environment.

4. The apparatus according to claim 1, wherein the control unit is configured to freeze the probe when the first sensor detects that the probe is not being operated.

5. The apparatus according to claim 1, wherein the control unit is further configured to control the state of operation of the ultrasound detecting system based on the detecting results of the first sensor.

6. The apparatus according to claim 1, wherein the control unit is further configured to freeze the probe when the first sensor detects that the probe is not being operated and when the second sensor detects that the user is not in proximity of the device main body.

7. The apparatus according to claim 6, wherein the control unit is further configured to set the ultrasound detecting system in a standby state when the first sensor detects that the probe is not being operated and when the second sensor detects that the user is not in proximity of the device main body.

8. An ultrasound detecting system comprising:
a device main body;
a probe connected to the device main body; and
an apparatus for automatically controlling a state of operation of the ultrasound detecting system, the apparatus comprising:
a first sensor disposed in the probe and connected to a device main body, wherein the first sensor is configured to detect if the probe is being operated;
a second sensor disposed in the device main body of the ultrasound detecting system, wherein the second sensor is configured to detect if a user is in proximity of the device main body; and
a control unit configured set the probe in an activated state when the first sensor detects that the probe is not being operated and when the second sensor detects that the user is in proximity of the device main body.

9. The ultrasound detecting system according to claim 8, wherein the control unit is further configured to control the state of operation of the ultrasound detecting system based on detecting results of the first sensor.

10. A method for automatically controlling a state of operation of an ultrasound detecting system, the method comprising:
    detecting, with a first sensor disposed in a probe of the ultrasound detecting system, if the probe is being operated;
    detecting, with a second sensor disposed in a device main body of the ultrasound detecting system, if a user is in proximity of the device main body; and
    automatically controlling the state of operation of the ultrasound detecting system by one of (i) setting the probe in an activated state when the first sensor detects that the probe is not being operated, and when the second sensor detects that the user is in proximity of the device main body, and (ii) freezing the probe if the first sensor detects that the probe is being operated and if the second sensor detects that the user is in proximity of the device main body.

11. The method according to claim 10, wherein detecting if the probe is being operated comprises detecting changes in capacitance between the probe and the ambient environment.

12. The method according to claim 10, wherein detecting if the probe is being operated comprises detecting changes in inductance between the probe and the ambient environment.

13. The method according to claim 10, wherein automatically controlling the state of operation of the ultrasound detecting system comprises freezing the probe if the first sensor detects that the probe is not being operated.

14. The method according to claim 10, wherein freezing the probe comprises setting the ultrasound detecting system in a standby state.

* * * * *

UNITED STATES PATENT AND TRADEMARK OFFICE
CERTIFICATE OF CORRECTION

PATENT NO. : 9,204,860 B2
APPLICATION NO. : 13/629672
DATED : December 8, 2015
INVENTOR(S) : Ji et al.

It is certified that error appears in the above-identified patent and that said Letters Patent is hereby corrected as shown below:

On the Title Page, in item (73), under "Assignee", in Column 1, Line 1,
delete "GE MEDICAL SYSTEMS" and
insert -- GE MEDICAL SYSTEMS GLOBAL --, therefor.

Signed and Sealed this
Sixteenth Day of August, 2016

Michelle K. Lee
*Director of the United States Patent and Trademark Office*